United States Patent
Schoenefeld

(10) Patent No.: US 6,709,433 B1
(45) Date of Patent: Mar. 23, 2004

(54) BRIDGING/NON-BRIDGING EXTERNAL BONE FIXATOR

(75) Inventor: Ryan J. Schoenefeld, Fort Wayne, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 10/028,810

(22) Filed: Dec. 20, 2001

(51) Int. Cl.[7] ............................................. A61B 17/66
(52) U.S. Cl. ........................... 606/57; 606/59; 606/54
(58) Field of Search .............................. 606/54, 55, 59, 606/56, 57, 58, 87, 86, 88, 72, 82, 102

(56) References Cited

U.S. PATENT DOCUMENTS

| | | |
|---|---|---|
| 1,789,060 A | 1/1931 | Weisenbach |
| 4,611,586 A | 9/1986 | Agee et al. |
| 4,730,608 A | 3/1988 | Schlein |
| 4,919,119 A * | 4/1990 | Jonsson et al. ............... 606/54 |
| 4,922,896 A | 5/1990 | Agee et al. |
| 5,376,091 A | 12/1994 | Hotchkiss et al. |
| 5,620,442 A | 4/1997 | Bailey et al. |
| 5,683,389 A | 11/1997 | Orsak |
| 5,891,144 A | 4/1999 | Mata et al. |
| 5,897,555 A | 4/1999 | Clyburn et al. |
| 5,951,556 A | 9/1999 | Faccioli et al. |
| 6,162,223 A | 12/2000 | Orsak et al. |
| 6,171,309 B1 | 1/2001 | Huebner |
| 6,197,027 B1 * | 3/2001 | Hajianpour ................... 606/59 |

OTHER PUBLICATIONS

Infante, Anthony F., Jr., D.O., Non–Bridging External Fixation of the Distal Radius, Nov. 10–12, 2000, pp. 9–1 to 9–3.

* cited by examiner

Primary Examiner—Cary E. O'Connor
Assistant Examiner—Candice C. Melson
(74) Attorney, Agent, or Firm—Harness, Dickey & Pierce, P.L.C.

(57) ABSTRACT

An external bridging/non-bridging bone fixation device including at least a first member and a second member. The first member is implanted substantially permanently on an arm bone during an entire healing process. Whereas the second member is adapted to be substantially temporarily implanted and affixed between the first member and a metacarpal of the associated hand. The second member may be a singular rigid piece or may be formed of several modular pieces affixed together. In particular, the second member may be hinged to allow for an offset or angled implantation. Also, the second member may include a plurality of pieces that are rigidly held together after implantation to allow for high selectivity by a physician. The bridging/non-bridging bone fixation device allows for a bridging adaptation during an initial portion of healing and a non-bridging adaptation during the extended healing process to reduce the possibility of stiffness and plaques due to prolonged periods of immobility.

26 Claims, 4 Drawing Sheets

BRIDGING/NON-BRIDGING EXTERNAL BONE FIXATOR

FIELD OF THE INVENTION

The present invention relates to an external bone fixator and more particularly to an external bone fixator that is selectively a bridging and non-bridging fixator.

BACKGROUND OF THE INVENTION

It is known in the art that bones should be fixed or aligned in a particular position or orientation after an injury and several different methods are used. One generally known method is to place a cast on the injured area using a material that hardens after application, such as a plaster cast. The use of such a plaster cast, however, generally completely immobilizes the portion of the anatomy about which it is placed. Additionally, such plaster casts are extremely large and bulky and can be rather heavy for a patient who must use the plaster cast.

Additional bone fixation devices known in the art include internal fixation plates or external fixators. Attachment devices, such as screws or pins, affix the plate fixators to the bone sections which must be held in place and fixed during the healing process. These internal plates and external fixators are generally of an unitary length and of a fixed construction not allowing any motion of the anatomy to which it is attached while it is in place throughout the entire healing process.

Additionally, bone fixation pins and screws, and other internal devices, that are simply lodged into a bone structure may also be used to hold a bone in a fixed position while it is healing. These devices ensure that the bone is held in the proper position during healing without permitting further trauma to the bone. Here again, the internal pins and screws also do not allow movement of the fixed or attached portions of anatomy once inserted.

Accordingly, most of these devices create complete immobility in the portion of the anatomy upon which they are placed during the recovery process. This complete immobilization of a portion of anatomy, especially when it is a joint or other moving part, can stiffen and injure the joint due to non-movement. Additionally, adjacent portions of the anatomy are often used to support the part which is healing, thereby immobilizing greater sections of the anatomy. In particular, if an arm or wrist injury occurs and a bone must be fixed during the recovery period, the loss of motion in the joint may increase pain and the possibility of injury after the fixation device has been removed. Therefore, it is desirable to have a fixation device which will allow some movement during a portion of the recovery process, while also ensuring proper immobilization of the body portion under recovery so that corrective healing may occur.

SUMMARY OF THE INVENTION

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The present invention relates to a convertible external bone fixator that converts between a bridging and non-bridging operation. The external bone fixator is made to fix bones relative to each other across a joint and then later allow movement of the joint by removing a first portion of the external bone fixator. The conversion from bridging to non-bridging operation is accomplished without detaching a second portion of the bridging/non-bridging bone fixation device.

A first embodiment includes an external bone fixation device for fixing a first bone and a second bone relative to one another in a predetermined orientation. The external bone fixation device includes a first bone fixation member that has a tail portion and a head portion each defining a plurality of bores and extending only along a portion of the length of the first bone. A connector extends from the first bone fixation member. A second bone fixation member has a proximal end and a distal end, wherein the proximal end is selectively affixed to the connector. A first selective attachment device selectively affixes the first bone fixation member to the first bone. A second selective attachment device selectively affixes the second bone fixation member to the second bone. When the first bone fixation member is selectively affixed to the first bone and the second bone fixation member is selectively affixed to both the connector and the second bone the first and second bones are substantially immobile.

A second embodiment of the present invention includes an external bone fixation device for fixing an arm bone, a wrist bone, and a metacarpal in a predetermined orientation. The external bone fixation device includes a first rigid bone fixation member, having a proximal tail portion and a distal head portion, defining a plurality of bores through said tail portion and said head portion. A holding mechanism extends from the distal head portion. A second bone fixation member selectively interconnects the holding mechanism and the metacarpal. A first attachment device selectively affixes the first bone fixation member to the arm bone. A second attachment device selectively affixes the second bone fixation member to the metacarpal. When the first bone fixation member is affixed to the arm bone and the second bone fixation member is selectively interconnected between said holding mechanism and the metacarpal, then the metacarpal is substantially immobile.

A third embodiment of the present invention includes an external bone fixation device for fixing an arm bone, a wrist bone, or a metacarpal in a predetermined orientation. The external bone fixation device includes a first rigid bone fixation member, having a proximal tail portion and a distal head portion having a side. The proximal tail portion defines a first plurality of bores formed longitudinally along said tail portion. The distal head portion defines a second plurality of bores in an array thereon, wherein at least a portion of the second plurality of bores are displaced laterally from the first plurality of bores. A mounting body extends from the side of the distal head portion. The second bone fixation member has a proximal end and a distal end, wherein a portion of the proximal end is received in said mounting body, and is selectively affixed in the mounting body. A first attachment device affixes the first bone fixation member to the arm bone. A second attachment device selectively affixes the second bone fixation member to the metacarpal. When the first bone fixation member is affixed to the arm bone and the second bone fixation member is selectively affixed to the metacarpal, and the second bone fixation member is selectively affixed in the clamp then the wrist and metacarpal are substantially immobile.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
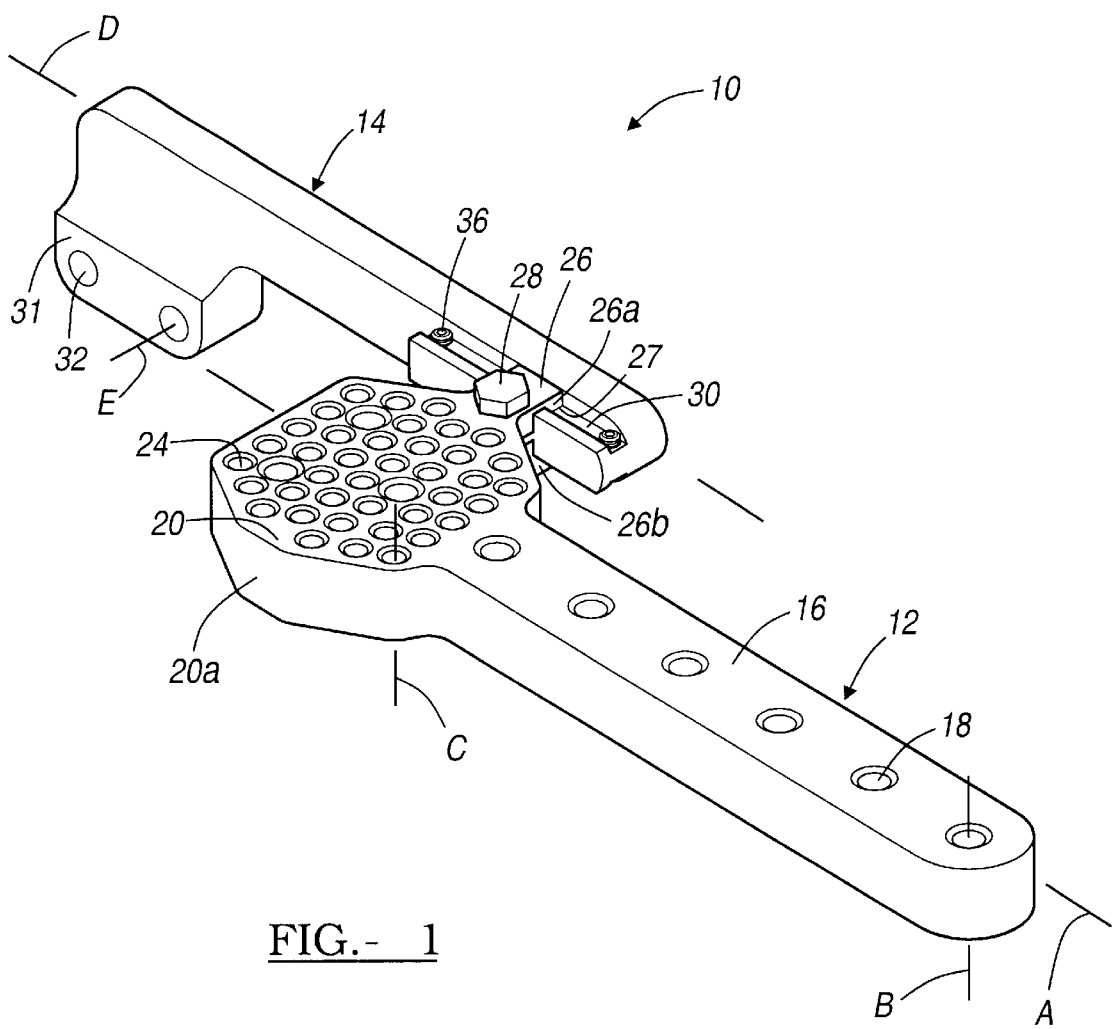
FIG. 1 is a perspective view of a bridging/non-bridging external bone fixation device.

With reference to FIG. 1, an external bone fixation device 10 of the present invention includes an arm fixation member 12 and a bridging member 14. The arm fixation member 12 is similar to that disclosed in commonly assigned U.S. Pat. No. 6,197,027, which is hereby incorporated by reference. The arm fixation member 12 includes a proximal arm or tail portion 16 which defines a plurality of arm bores 18 along its longitudinal axis A. Even though arm bores 18 are formed along the longitudinal axis A of the arm portion 16, they extend through the arm portion 16, therefore, the central axes B of the arm bores 18 are perpendicular to the longitudinal axis A of the arm portion 16. At the distal end of the arm fixation member 12 is a larger block or platter area 20 that defines a plurality of platter bores 24, each adapted to receive a pin or other fixation device further discussed herein. The platter area 20 has a width greater than the width of the arm portion 16. Thus, an exterior edge 20a of the platter area 20 is laterally offset from the longitudinal axis A of the arm portion 16. The platter bores 24 cover a substantial area of the platter area 20 and define an array or pattern that extends beyond the longitudinal axis A of the arm portion 16. Therefore, pins or other fixation devices that are inserted into platter bores 24 may be laterally offset from fixation or attachment devices inserted through arm bores 18. Nevertheless, the central axis C of the platter bores 24 and the central axis B of the arm bores 18 are substantially parallel to each other. Extending from the exterior edge 20a of the platter area 20 is a mounting area or block 26 defining a channel 27. The mounting block 26 extends from the platter area 20 and is generally integrally formed therewith. It will be understood that the mounting block 26 is laterally offset from the longitudinal axis A of the arm portion 16 since the exterior edge 20a of the platter area 20 is also offset. The mounting block 26 acts as a holding mechanism or a clamp and has a top portion 26a and a bottom portion 26b which are separated from each other except at the ends that meet with the platter area 20. A screw 28 or other suitable locking device engages threads in the mounting block 26 to adjust the size of the channel 27 so that the mounting block 26 holds bridging member 14 in a pre-determined position.

In this first embodiment, the bridging member 14 is a single, long rigid piece which includes a track 30 extending from a medial side of the bridging member 14. The track 30 is slideably engaged in the channel 27 of the mounting block 26 and held in a pre-determined position. The track 30 is held in the mounting block when the screw 28 is tightened to pull the top portion 26a and the bottom portion 26b of mounting block 26 together. In this way, the bridging member 14 and the arm fixation member 12 are held in a pre-determined and fixed position. According to the first embodiment, the bridging member 14 and the arm fixation member 12 are held generally parallel to each other although the central longitudinal axis D of the bridging member 14 is laterally offset from the arm portion 16, due to the size of the platter area 20. Therefore, the central longitudinal axis D of the bridging member 14 is laterally offset to the central longitudinal axis A of the arm portion 16, although the bridging member 14 and the arm fixation member 12 are substantially parallel to each other. At the distal end of the bridging member 14 is a metacarpal block 31. The metacarpal block 31 defines a plurality of metacarpal bores 32 formed transversely there through. Since the metacarpal bores 32 are formed transversely to the bridging member 14, they have a central axis E substantially perpendicular to the platter bores 24 and the arm bores 18. Thus, attachment members received in the metacarpal bores 32 would also extend substantially perpendicular to attachment members A received in platter bores 24 or arm bores 18. As described herein, pins may engage metacarpals through the metacarpal bores 32 to ensure that the metacarpals are held fixed relative to the bridging member 14.

It will also be understood that in an alternative embodiment, the track 30 may extend from the bridging member 14 at a plurality of angles. Such an angled track 30 may be used to account for the uniqueness of a particular patient's anatomy. If the track 30 is formed at an angle, then the bridging member 14 is held relative to the arm fixation member 12 at an angle. Even when the track 30 is formed at an angle from the bridging member 14, the central longitudinal axis of the bridging member 14 would still be generally parallel to the central longitudinal axis of the arm fixation member 12. When the track 30 is formed at an angle, the metacarpal block 31 and the metacarpal bores 32 would have an angle substantially equal to the angle of the track 30. Therefore, the attachment members that are received in the metacarpal bores 32 would be at an angle other than perpendicular to the attachment members received in platter bores 24 and arm bores 18.

An alternative embodiment includes the track 30 having stops 36 along the track 30 to allow limited movement of the hand during the healing process. The stops 36 may include several different embodiments, but for example may be set screws. The set screws could be inserted through tapped bores in either edge of the track 30 or in tapped bores in the track 30 itself to stop the movement of the bridging member 14 by engaging the top portion 26a or the bottom portion 26b of the mounting block 26. In this way, stops 36 may be inserted at some point after implantation of the bridging/non-bridging bone fixation device 10 to allow a limited range of motion without completely removing the bridging member 14. If stops 36 are included on the track 30, the bridging member 14 can slide in the mounting block 26 a limited and pre-determined amount of movement of the metacarpal 48 without allowing the unlimited movement of the same by simply removing the bridging member 14. It will be understood that the stops 36 could be any number of mechanisms such as bumps or raised portions on the track 30.

Figure 2A:
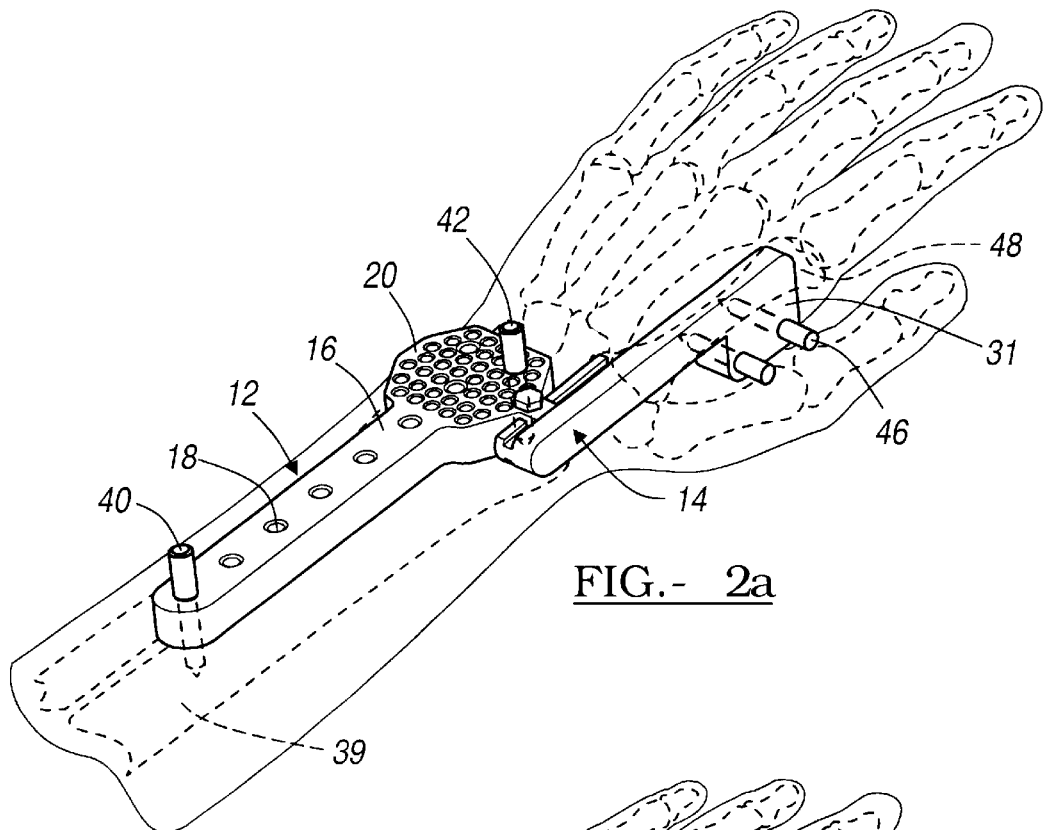
FIG. 2a is a perspective view of the bridging/non-bridging external bone fixation device implanted in the bridging orientation.

With particular reference to FIG. 2a, the bridging/non-bridging bone fixation device 10 of the present invention is shown after implantation onto a human appendage. The bridging/non-bridging bone fixation device 10 is initially implanted in the bridged formation. The bridged formation includes the arm fixation member 12 affixed to an arm bone 39 with at least one attachment device or a pin 40. The pins 40, and other pins discussed herein, may be held to the bridging/non-bridging bone fixation device 10 through any conventional means such as a cannulated bolt. Pins 40 are inserted through the arm bores 18 of the arm portion 16 as needed to hold the arm fixation member 12 in place. Additional pins 42 are be placed in the platter bores 24 of the platter area 20 at the proximal end of the arm fixation member 12. The pins 42 engage the distal end of the arm bone 39 to hold secure the arm fixation member 12. Pins 40 and 42 are inserted through the arm fixation member 12 substantially parallel to one another. Regardless of whether they are inserted in arm bores 18 or platter bores 24. Due to the array of the platter bores 24, however, the pin 42 that is inserted in the platter bores 24 may be inserted laterally offset relative to the pin 40 inserted in arm bore 18. This will ensure a fixed and substantially solid attachment of the arm fixation member 12 to the arm bone 39. Furthermore, if the distal end of the arm bone 39 is fractured into more than one piece, additional pins 42 may be inserted in additional platter bores 24 to engage each portion of fractured bone to hold it in place. To complete the bridging orientation, the bridging member 14 is put in place and locked relative to the arm fixation member 12 by clamping the mounting block 26 with screw 28 onto track 30. Additional pins 46 are inserted through the metacarpal bores 32 of the metacarpal block 31 to hold at least a metacarpal 48, or a portion of the digits, in a predetermined orientation. The pins 46 in the metacarpal block 31 extend substantially perpendicular to the pins 40 and 42 which are inserted through the arm fixation member 12. This allows the pins 46 received through the metacarpal bores 32 to engage the metacarpal 48 laterally rather than in line with the pins 40 and 42 which are received in the arm fixation member 12. This allows for a stable and secure external fixation of the arm bone 39 and the metacarpal 48 relative to each other. Thus, the bridging orientation, shown particularly in FIG. 2a, is used to lock the arm bone 39, wrist, and certain metacarpals 48 in a predetermined orientation.

Figure 2B:
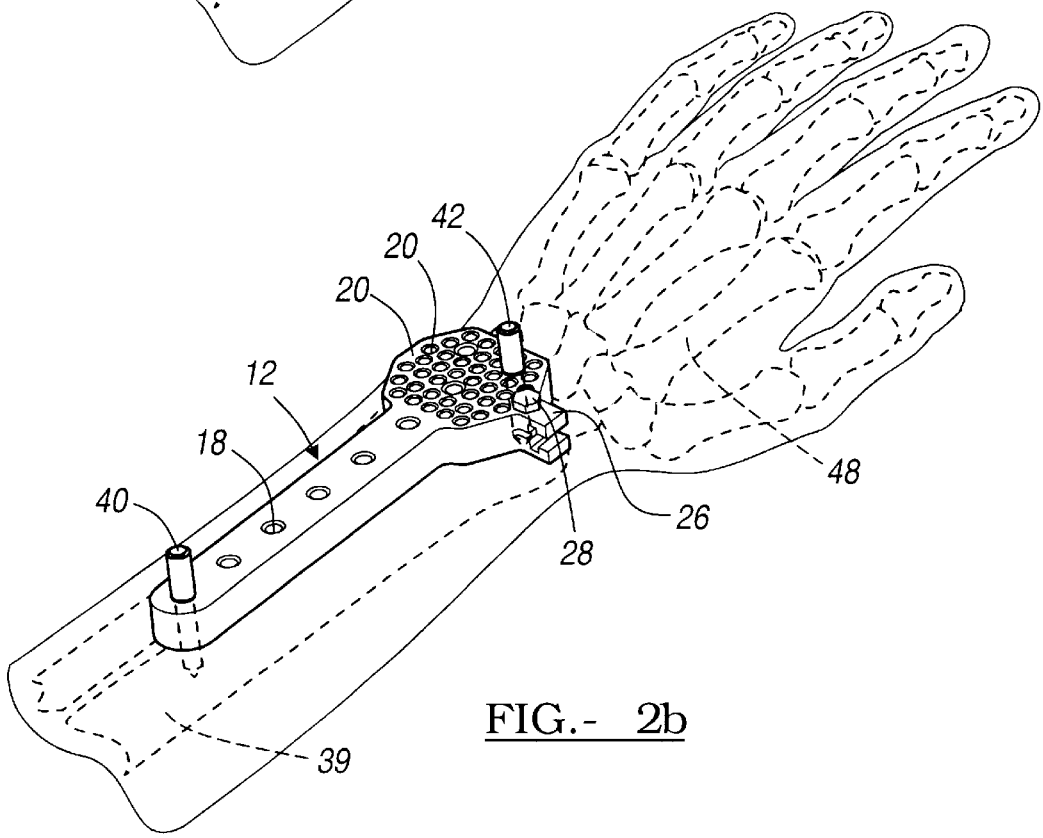
FIG. 2b is a perspective view of the bridging/non-bridging external bone fixation device implanted in the non-bridging orientation.

During the initial stages of healing, the bridged formation is used to help ensure a completely immobile wrist and hand. After it has been determined that enough initial healing has occurred, so that movement of the digits and wrist may occur safely, then the bridging member 14 may be removed while not disturbing the arm fixation member 12. As shown particularly in FIG. 2b, the non-bridging orientation is achieved by removing pins 46 and unlocking mounting block 26 and removing the bridging member 14. After this occurs, the metacarpal 48 and most of the wrist bones may move freely. Though complete range of motion may not be restored, greater motion is allowed. This is not to say that arm fixation member 12 may not be positioned so as to allow full range of motion of the wrist and digits after removing the bridging member 14. The arm fixation member 12 is never moved or removed during the non-bridging operation of the non-bridging/bridging bone fixation device 10. The pins 46 are removed from the metacarpal 48 and then the mounting block 26 is loosened and the bridging member 14 is removed. Therefore, the arm fixation member 12 may be left undisturbed to continue holding the arm bone 39 in a particular orientation. This helps to ensure that stiffness, plaques or other conditions are reduced in the wrist and hand as opposed to locking all of the bones and moving parts of the hand and wrist during the entire healing process.

Figure 3:
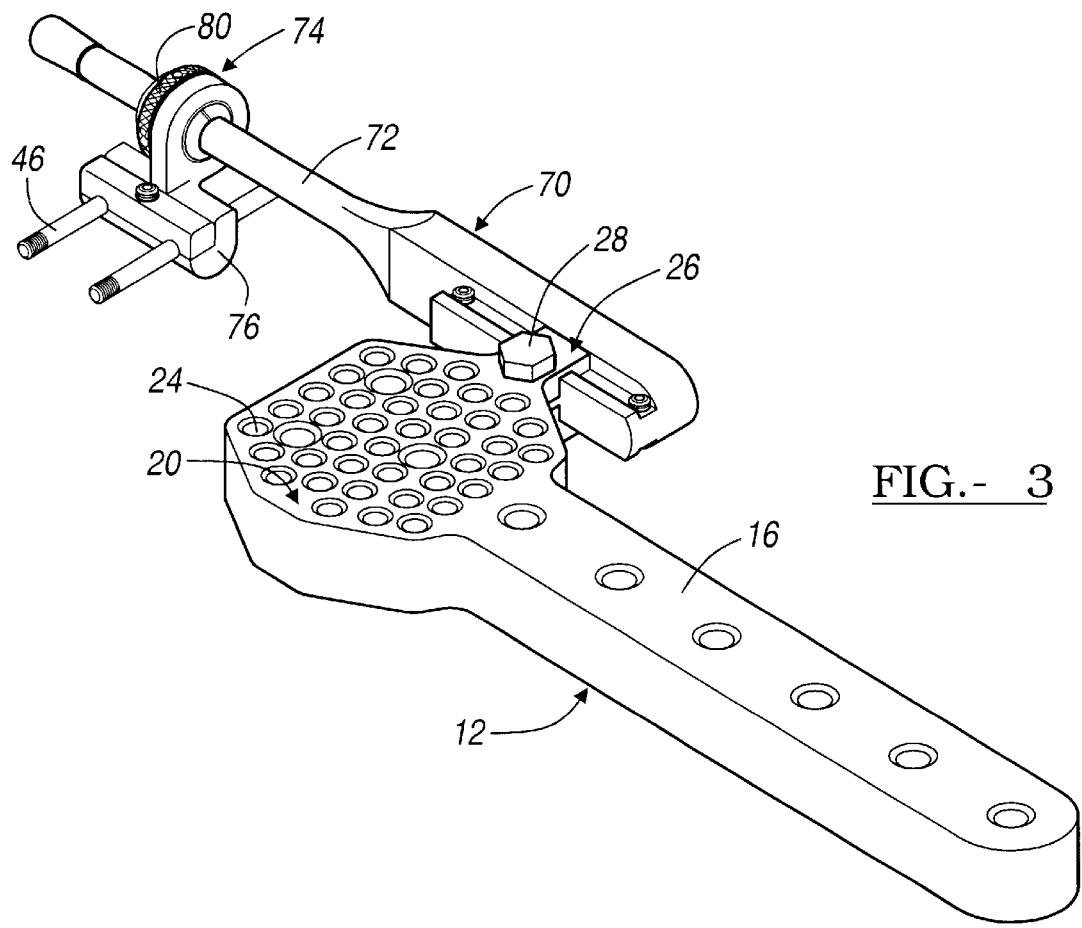
FIG. 3 is a perspective view of a bridging/non-bridging external bone fixation device including a pin clamp according to a second embodiment of the present invention.
Figure 4:
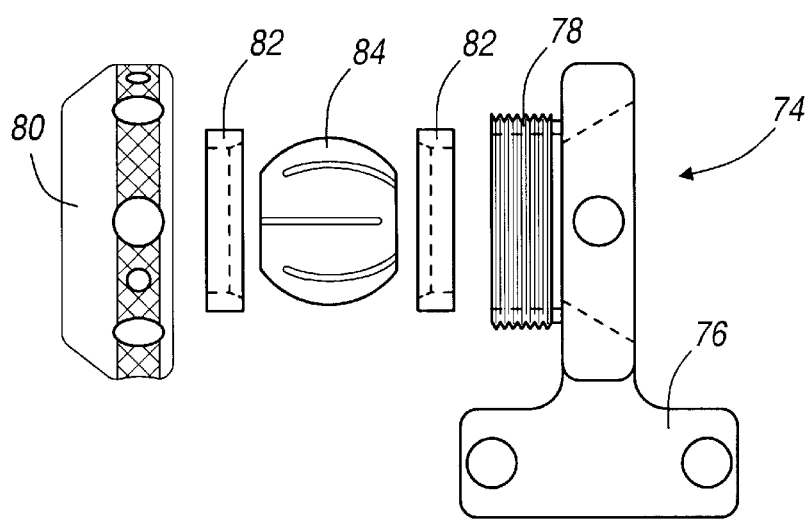
FIG. 4 is an exploded view of the pin clamp shown in FIG. 3.

With reference to FIGS. 3 and 4, where like numerals reference like portions discussed in relation to the previous embodiments, a third alternative embodiment includes a modular bridging member 70 that tapers to a round bar at a distal end 72 of the bridging member 70. The pins 46 that are inserted into the metacarpal 48 are first affixed to a pin clamp 74 which is clamped onto the distal end 72 of the bridging member 70. The pin clamp 74 is similar to the clamp disclosed in co-pending patent application having a Ser. No. 09/790,770 to Ryan J. Schoenefeld and commonly assigned, which is incorporated herein by reference. With reference to FIG. 4, the pin clamp 74 generally includes a pin retaining portion 76 which has a threaded portion 78 extending therefrom. An internally threaded portion 80 affixes to threaded portion 78. Held in between internally threaded portion 80 and the threaded portion 78 are two washer portions 82 and a ball joint 84. The distal end 72 of the bridging member 70 is received through the center portion of the threaded portion 78, the ball joint 84 and the internally threaded portion 80. When the internally threaded portion 80 is engaged on the threaded portion 78, the bail joint 84 is held in a predetermined position. The internal ball joint 84 allows for certain degrees of freedom in the orientation of the pin retaining portion 76 relative to the distal end 72. Therefore, pins 46 may be orientated relative to the bridging member 70 to allow greater freedom of implanting the pins 46 when implanting the bridging/non-bridging bone fixation device 10 depending upon the particular anatomy or situation of the patient.

Figure 5:
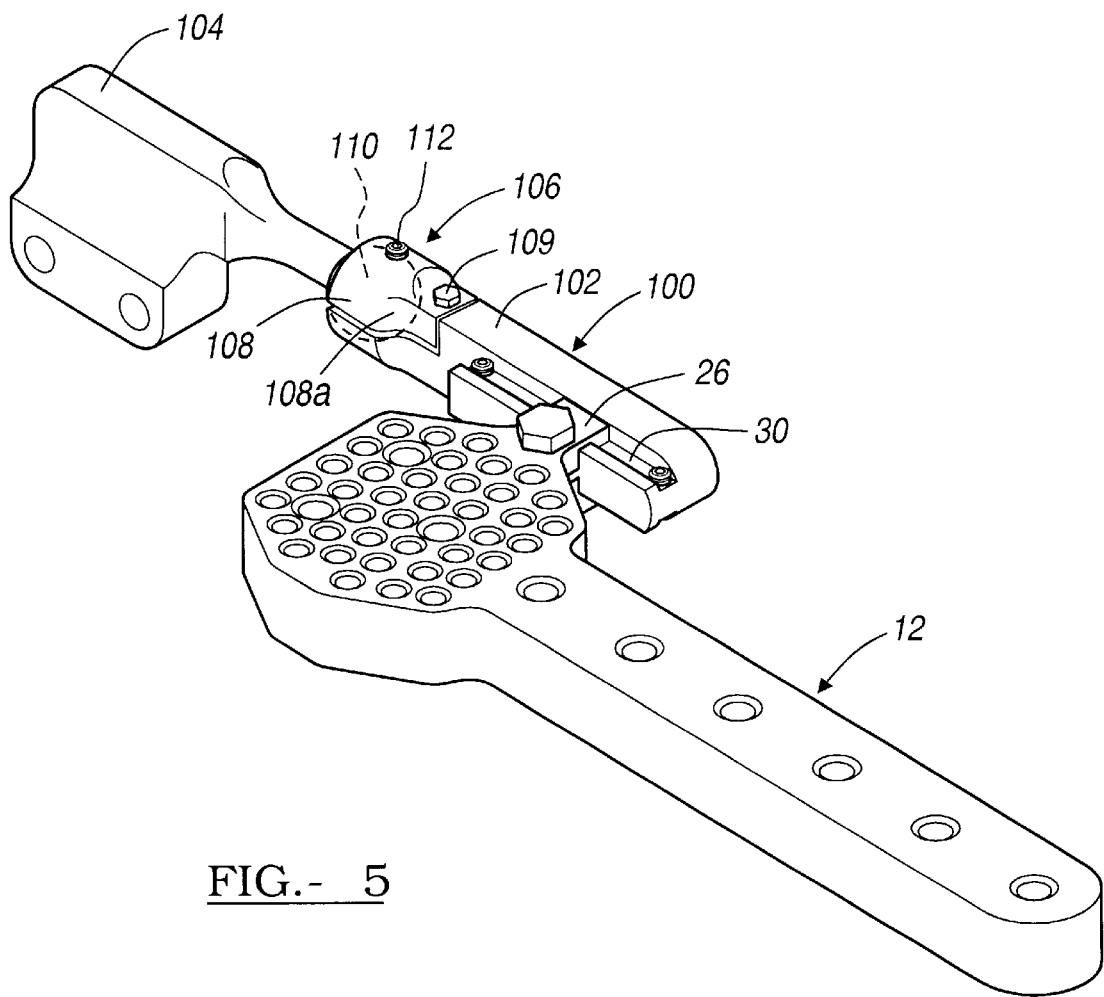
FIG. 5 is a perspective view of a bridging/non-bridging external bone fixation device including a hinged bridging member according to a third embodiment of the present invention.

A fourth alternative embodiment, shown in FIG. 5 where like numerals reference like portions discussed in relation to the previous embodiments, includes a bridging member 100 that is, at least initially, non-rigid. The bridging member 100 includes at least two portions a proximal portion 102 and a distal portion 104 interconnected with a ball joint 106. The distal end of the proximal portion 102 is a ball socket 108 which receives a ball 110 which extends from the proximal end of the distal portion 104. The ball socket 108 engages the ball 110 by locking engaging member 108a in place with a screw 109. The ball 110 is received within the ball socket 108 and may rotate in many degrees of freedom and is locked in place with set screw 112 once a proper orientation is gained. It will be understood that any other appropriate device may be used to lock the ball joint 106 in a proper orientation. Metacarpal pins 46 are then received through metacarpal bores 32 to engage a metacarpal 48. This also allows a physician greater flexibility during the implantation of the bridging/non-bridging bone fixation device 10.

It will also be understood that the alternative embodiment disclosed above may be combined in any number of combinations to achieve the spirit of the present invention while also allowing a great variety options to the physician implanting the bridging/non-bridging bone fixation device 10. It will also be understood that the bridging/non-bridging bone fixation device 10 may be affixed to the patient in a plurality of ways. Pins 40, 42, 46 may alternatively, for example, be screws. The pins 40, 42, 46 may also include threads or ridges that assist in affixing the pin 40, 42, 46 to the bone structure. Also, the pin 40 may differ from the pin 42 or the pin 46. Any appropriate device may be used to affix the bridging/non-bridging bone fixation device 10 to the patient.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An external bone fixation device for fixing a first bone and a second bone relative to one another in a predetermined orientation, the external bone fixation device comprising:
   a first bone fixation member having a tail portion and a head portion defining a plurality of bores and extending only along a portion of the length of the first bone;
   a connector extending from said first bone fixation member;
   a second bone fixation member having a proximal end and a distal end, wherein said proximal end may be selectively affixed to said connector;
   a first selective attachment device adapted to selectively affix said first bone fixation member to the first bone; and
   a second selective attachment device adapted to selectively affix said second bone fixation member to the second bone, wherein when said first bone fixation member is selectively affixed to the first bone and said second bone fixation member is selectively affixed to both said connector and the second bone, the first and second bones are substantially immobile;
   wherein said plurality of bores includes a first set of bores and a second set of bores, wherein said first set of bores are aligned along said tail portion and said second set of bores form an array in said head portion.

2. The external bone fixation device of claim 1, further comprising;
   a track extending from said second bone fixation member to engage said connector; and
   wherein engagement of said track with said connector operates to selectively affix said first bone fixation member to said second bone fixation member.

3. The external bone fixation device of claim 2, wherein said track includes a first stop and a second stop wherein second bone fixation member slides along said track between said first stop and said second stop to allow movement of said second bone fixation member relative to said first bone fixation member.

4. The external bone fixation device of claim 2, wherein said track extends from said second bone fixation member at a predetermined angle so that said second bone fixation member is able to selectively engage said first bone fixation member at said predetermined angle.

5. The external bone fixation device of claim 1, wherein said first bone fixation member is substantially rigid.

6. The external bone fixation device of claim 1, wherein said first attachment device includes a plurality of said first attachment devices each received in one of said plurality of bores substantially parallel to one another.

7. The external bone fixation device of claim 1, wherein said first bone fixation member and said second bone fixation member each define bores, and wherein said first attachment device and said second attachment device are pins which are received through said bores and held in bone.

8. The external bone fixation device of claim 1, wherein said second bone fixation member comprises a plurality of operably interconnected members forming said second bone fixation member, wherein said second bone fixation member is orientatable independent of and relative to said first bone fixation member.

9. The external bone fixation device of claim 1, further comprising a second attachment device holding mechanism, wherein said second attachment device holding mechanism allows the independent orientation of said second attachment device relative to said second bone fixation member.

10. The external bone fixation device of claim 1, wherein when said second bone fixation member is selectively not affixed to said connector the first and second bones are moveable relative to one another.

11. The external bone fixation device of claim 1, further comprising:
    a ball joint selectively positionable in a plurality of positions;
    a locking mechanism to lock said ball joint in a particular position; and
    wherein said second bone fixation member includes a first portion and a second portion and said ball joint operably interconnects said first portion and said second portion such that said first portion and said second portion are positionable relative to each other.

12. An external bone fixation device for fixing an arm bone, a wrist bone, and a metacarpal in a predetermined orientation, the external bone fixation device comprising:
    a first rigid bone fixation member, having a proximal tail portion and a distal head portion, defining a plurality of bores through said tail portion and said head portion;
    a holding mechanism which extends from said distal head portion;
    a second bone fixation member adapted to selectively interconnect said holding mechanism and the metacarpal;
    a first attachment device adapted to selectively affix said first bone fixation member to the arm bone; and
    a second attachment device adapted to selectively affix said second bone fixation member to the metacarpal;
    wherein when the first bone fixation member is affixed to the arm bone and the second bone fixation member is selectively interconnected between said holding mechanism and the metacarpal, the metacarpal is substantially immobile;
    wherein said holding mechanism is operable to rigidly interconnect said first rigid bone fixation member and said second bone fixation member;
    wherein a first sub-plurality of the bores are aligned in said tail portion and a second sub-plurality of the bores are arrayed in said head portion.

13. The external bone fixation device of claim 12, further comprising:
    a track extending from said second bone fixation member which engages said holding mechanism; and
    wherein an engagement of said track in said holding mechanism creates said selective engagement of said first bone fixation member with said second bone fixation member.

14. The external bone fixation device of claim 13, wherein said track includes a first stop and a second stop wherein second bone fixation member slides along said track between said first stop and said second stop to allow movement of said second bone fixation member relative to said first bone fixation member.

15. The external bone fixation device of claim 13, wherein said track extends from said second bone fixation member at a predetermined angle so that said second bone fixation member is able to selectively engage said first bone fixation member at said predetermined angle.

16. The external bone fixation device of claim 12, wherein said first, bone fixation member is rigidly formed and is adapted to hold substantially fixed the arm bone.

17. The external bone fixation device of claim 12, further comprising:
- a ball joint selectively positionable in a plurality of positions;
- a locking mechanism to lock said ball joint in a particular position; and
- wherein said second bone fixation member includes a first portion and a second portion and said ball joint operably interconnects said first portion and said second portion such that said first portion and said second portion are positionable relative to each other.

18. The external bone fixation device of claim 12, further comprising a second attachment device holding mechanism, wherein said second attachment device holding mechanism allows the independent orientation of said second attachment device relative to said second bone fixation member.

19. An external bone fixation device for fixing an arm bone, a wrist bone, and a metacarpal in a predetermined orientation, the external bone fixation device comprising:
- a first rigid bone fixation member, having a proximal tail portion and a distal head portion, defining a plurality of bores through said tail portion and said head portion;
- a holding mechanism which extends from said distal head portion;
- a second bone fixation member adapted to selectively interconnect said holding mechanism and the metacarpal;
- a first attachment device adapted to selectively affix said first bone fixation member to the arm bone; and
- a second attachment device adapted to selectively affix said second bone fixation member to the metacarpal; wherein when the first bone fixation member is affixed to the arm bone and the second bone fixation member is selectively interconnected between said holding mechanism and the metacarpal, the metacarpal is substantially immobile;
- wherein at least a portion of said plurality of bores defined by said head portion are laterally offset from said plurality of bores defined by said tail portion and wherein said first attachment device and said second attachment device are pins adapted to be received through said plurality of bores and held in bone.

20. An external bone fixation device for fixing an arm bone, a wrist bone, or a metacarpal in a predetermined orientation, the external bone fixation device comprising:
- a first rigid bone fixation member, having a proximal tail portion and a distal head portion having a side,
  - said proximal tail portion defining a first plurality of bores formed longitudinally along said tail portion;
  - said distal head portion defining a second plurality of bores in an array thereon, wherein at least a portion of said second plurality of bores are displaced laterally from said first plurality of bores;
- a mounting body extending from said side of said distal head portion;
- a second bone fixation member having a proximal end and a distal end, wherein a portion of said proximal end is received in said mounting body, and is selectively affixed in said mounting body;
- a first attachment device adapted to affix said first bone fixation member to the arm bone; and
- a second attachment device adapted to selectively affix said second bone fixation member to the metacarpal; wherein when said first bone fixation member is affixed to the arm bone and said second bone fixation member is selectively affixed to the metacarpal and said proximal end of said second bone fixation member is selectively affixed in said mounting body, the wrist and metacarpal are substantially immobile.

21. The external bone fixation device of claim 20, further comprising a track extending from said proximal end of said second bone fixation member, wherein said track is held in said mounting body to affix said second bone fixation member to said first bone fixation member.

22. The external bone fixation device of claim 21, wherein said track extends at an angle normal to said proximal end of said second bone fixation member.

23. The external bone fixation device of claim 21, wherein said track includes a first stop and a second stop wherein second bone fixation member slides along said track between said first stop and said second stop to allow movement of said second bone fixation member relative to said first bone fixation member.

24. The external bone fixation device of claim 20, further comprising;
- a ball joint selectively positionable in a plurality of positions;
- a locking mechanism to lock said ball joint in a particular position; and
- wherein said second bone fixation member includes a first portion and a second portion and said ball joint operably interconnects said first portion and said second portion such that said first portion and said second portion are positionable relative to each other.

25. The external bone fixation device of claim 20, wherein said first attachment device and said second attachment device are pins adapted to be held in bone, and wherein said pins are received through said bores.

26. The external bone fixation device of claim 20, further comprising a second attachment device holding mechanism, wherein said second attachment device holding mechanism allows the independent orientation of said second attachment device relative to said second bone fixation member.

* * * * *